United States Patent
Meng et al.

(10) Patent No.: US 10,337,972 B2
(45) Date of Patent: Jul. 2, 2019

(54) HIGH-SPEED RHEOMETER

(71) Applicant: Tsinghua University, Beijing (CN)

(72) Inventors: Yonggang Meng, Beijing (CN); Xiang Yu, Beijing (CN); Yu Tian, Beijing (CN); Jun Zhang, Beijing (CN)

(73) Assignee: TSINGHUA UNIVERSITY, Beijing (CN)

( * ) Notice: Subject to any disclaimer, the term of this patent is extended or adjusted under 35 U.S.C. 154(b) by 283 days.

(21) Appl. No.: 15/300,633

(22) PCT Filed: Apr. 7, 2015

(86) PCT No.: PCT/CN2015/075982
§ 371 (c)(1),
(2) Date: Sep. 29, 2016

(87) PCT Pub. No.: WO2015/154651
PCT Pub. Date: Oct. 15, 2015

(65) Prior Publication Data
US 2017/0108422 A1 Apr. 20, 2017

(30) Foreign Application Priority Data
Apr. 8, 2014 (CN) .......................... 2014 1 0138965

(51) Int. Cl.
*G01N 11/14* (2006.01)

(52) U.S. Cl.
CPC .................... *G01N 11/142* (2013.01)

(58) Field of Classification Search
CPC .................................................. G01N 11/142
See application file for complete search history.

(56) References Cited

U.S. PATENT DOCUMENTS 3,667,286 A * 6/1972 Kaufman ............... G01N 11/14
73/54.29
3,751,975 A * 8/1973 Katsura .................. G01N 11/14
73/54.38

(Continued)

FOREIGN PATENT DOCUMENTS

CN      101308076      11/2008
CN      101592581      12/2009

(Continued)

OTHER PUBLICATIONS

SIPO, First Office Action for CN Application No. 201410138965, dated Sep. 11, 2015.

(Continued)

*Primary Examiner* — John Fitzgerald
(74) *Attorney, Agent, or Firm* — Hodgson Russ LLP

(57) ABSTRACT

A high-speed rheometer includes a base, a driving device disposed on the base, a lower sample assembly connected with the driving device, an upper sample assembly disposed above the lower sample assembly, a torsion bar disposed on the upper sample assembly and being torsional upon the rotation of the upper sample assembly, and an optical torque measuring assembly. The lower sample assembly is rotatable under the driving of the driving device, and the upper sample assembly is rotatable under the driving of the fluid. The optical torque measuring assembly is used to measure a torsion angle of the torsion bar so as to obtain a torque generated during shearing the fluid to be tested.

13 Claims, 3 Drawing Sheets

(56) References Cited

U.S. PATENT DOCUMENTS

| | | | | |
|---|---|---|---|---|
| 4,202,204 A * | 5/1980 | Hartert | ............... | G01N 11/162 |
| | | | | 73/64.42 |
| 4,343,190 A | 8/1982 | Danko et al. | | |
| 4,726,220 A * | 2/1988 | Feier | ............... | G01N 11/14 |
| | | | | 73/54.28 |
| 5,228,331 A * | 7/1993 | Odagiri | ............... | G01N 11/162 |
| | | | | 73/54.41 |
| 5,610,325 A * | 3/1997 | Rajagopal | ............ | G01N 11/142 |
| | | | | 73/54.35 |
| 5,705,810 A | 1/1998 | Wang et al. | | |
| 6,776,028 B1 | 8/2004 | Lukay | | |
| 6,978,662 B2 * | 12/2005 | Platzek | ............... | G01N 11/14 |
| | | | | 73/54.01 |
| 7,275,419 B2 * | 10/2007 | Raffer | ............... | G01N 11/142 |
| | | | | 73/54.01 |
| 7,500,385 B2 * | 3/2009 | Liberatore | .......... | G01N 11/142 |
| | | | | 73/54.23 |
| 7,526,941 B2 * | 5/2009 | Doe | ............... | G01N 11/14 |
| | | | | 73/1.02 |
| 7,594,429 B2 * | 9/2009 | Liberatore | ............ | G01N 11/14 |
| | | | | 73/54.23 |
| 8,763,447 B2 * | 7/2014 | Nagoshi | ............... | G01N 11/142 |
| | | | | 73/54.02 |
| 9,267,871 B2 * | 2/2016 | Sierro | ............... | G01N 11/165 |
| 2007/0193343 A1 * | 8/2007 | Liberatore | ............ | G01N 11/14 |
| | | | | 73/54.33 |
| 2007/0295055 A1 * | 12/2007 | Doe | ............... | G01N 11/14 |
| | | | | 73/1.02 |
| 2011/0252871 A1 * | 10/2011 | Nagoshi | ............... | G01N 11/142 |
| | | | | 73/54.02 |
| 2012/0111097 A1 | 5/2012 | Sierro | | |
| 2013/0245968 A1 * | 9/2013 | Searle | ............... | G01N 11/14 |
| | | | | 702/50 |
| 2015/0345937 A1 * | 12/2015 | Seitz | ............... | G01B 21/042 |
| | | | | 250/231.13 |

FOREIGN PATENT DOCUMENTS

| | | |
|---|---|---|
| CN | 101692033 | 4/2010 |
| CN | 101750175 | 6/2010 |
| CN | 101923033 | 12/2010 |
| CN | 102112861 | 6/2011 |
| CN | 102706800 | 10/2012 |
| CN | 102830041 | 12/2012 |

OTHER PUBLICATIONS

Wang et al., "An approach to relationship between over-stress behavior and forming mechanism of viscous debris flow surges", The Chinese Journal of Geological Hazard and Control, vol. 11, No. 3, Sep. 2000, pp. 53-57.

WIPO, English translation of the ISR/WO for PCT/CN2015/075982, dated Jul. 17, 2015.

* cited by examiner

HIGH-SPEED RHEOMETER

CROSS-REFERENCE TO RELATED APPLICATION

The present application is a national phase entry under 35 USC § 371 of International Application PCT/CN2015/075982, filed Apr. 7, 2015, which claims the benefit of and priority to Chinese Patent Application No. 201410138965.7 filed Apr. 8, 2014, the entire disclosure of which is incorporated herein by reference.

FIELD

Embodiments of the present disclosure relate to measuring instruments, and more particularly to a high-speed rheometer.

BACKGROUND

Currently, rheological behaviors of fluids and characteristic parameters thereof are mainly measured by rheometers. The main object of a commercial rheometer is to test rheological behaviors of a medium, to optimize parameters of the medium in different operation conditions, and to verify a rheological constitutive equation theory. Traditional rheometers include capillary type rheometer, rotating rheometer, oscillating rheometer, stable state rheometer, and solid state rheometer. However, an existing rotation rheometer generally has a highest rotation speed of 5000 rpm, and a shearing rate thereof is hard to achieve $1 \times 10^4$/s. Although a capillary type rheometer may have a shearing rate up to about $1 \times 10^4$/s, it cannot test influences of different surfaces on the movements. Therefore, both rheometers cannot test in high shearing rate conditions. The ultra-shear viscometer from PCS company may measure shearing rates ranging from $1 \times 10^6$/s to $1 \times 10^7$/s, however, it cannot measure viscosities under relatively lower shearing rate conditions. Consequently, a rheometer having a relatively wider measuring range and being accurate at high shearing rates is needed.

The measuring method of a traditional rheometer generally uses stress-strain sensors or torque motors, which is limited by the accuracy of the sensor and has relatively lower measuring accuracy and relatively narrower measuring range, for example, two or three orders of magnitude. The gap control of a conventional rheometer is generally achieved by using a motor, which not only has large noise, but also has low control accuracy. Worse still, relatively smaller gaps are hard to obtain.

SUMMARY

Embodiments of the present disclosure seek to solve at least one of the problems existing in the prior art. Accordingly, embodiments of the present disclosure provide a high-speed rheometer having high measuring accuracy and large measuring range.

A high-speed rheometer according to embodiments of the present disclosure includes: a base; a driving device disposed on the base; a lower sample assembly connected with the driving device and being rotatable under the driving of the driving device, fluid to be tested being disposed on the lower sample assembly; an upper sample assembly disposed above the lower sample assembly and adapted to contact with the fluid to be tested, the upper sample assembly being rotatable under the driving of the fluid; a torsion bar disposed on the upper sample assembly and being torsional upon the rotation of the upper sample assembly; and an optical torque measuring assembly configured to measure a torsion angle of the torsion bar so as to obtain a torque generated during shearing the fluid to be tested.

With the high-speed rheometer according to embodiments of the present embodiment, the driving device drives the lower sample assembly and the fluid to be tested to rotate, and the upper sample assembly contacted with the fluid to be tested rotates accordingly. Therefore, the torsion bar connected with the upper sample assembly is driven to twist, and the optical torque measuring assembly may measure the torsion angle of the torsion bar, so as to obtain the torque generated by the fluid to be tested. A fact that the torque of the fluid to be tested is measured by using an optical measuring method not only improves the measuring accuracy of the high-speed rheometer, but also broadens the measuring range or measuring span. Specifically, the measuring range of the shearing rate may be increased by several orders of magnitude, which may cover both the low rate area and the high rate area.

In addition, the high-speed rheometer according to embodiments of the present disclosure may further have following additional features.

According to an embodiment of the present disclosure, the optical torque measuring assembly includes: a prism coaxially disposed on the torsion bar; a light source configured to emit light toward a side surface of the prism to form first reflected light; and a four-quadrant detector configured to receive the first reflected light.

According to an embodiment of the present disclosure, the optical torque measuring assembly further includes at least one reflector configured to receive the first reflected light, to generate second reflected light and to send the second reflected light to the four-quadrant detector.

According to an embodiment of the present disclosure, the four-quadrant detector has a predetermined position at which the first reflected light and the second reflected light arrive when the prism is not twisted, the four-quadrant detector is further configured to receive reflected lights from the prism before and after rotation of the prism and to generate a voltage difference, and the optical torque measuring assembly further includes: a feedback circuit configured to amplify the voltage difference to obtain an amplifying signal; and a piezoceramic deflection platform disposed on the at least one reflector and configured to receive the amplifying signal and to drive the reflector to deflect, such that the reflected light from the reflector arrives at the predetermined position.

According to an embodiment of the present disclosure, the at least one reflector includes first to fourth reflectors, and the piezoceramic deflection platform is disposed on the first reflector.

According to an embodiment of the present disclosure, the high-speed rheometer further includes: an upper sample carrier disposed on the base; and a manual displacement platform disposed on the upper sample carrier and connected with the upper sample assembly, the manual displacement platform being configured to adjust position of the upper sample assembly in an upper-down direction.

According to an embodiment of the present disclosure, the high-speed rheometer further includes: a piezoceramic displacement platform disposed below and connected with the manual displacement platform; and a distance measuring bar disposed on the torsion bar along a horizontal direction and connected with the piezoceramic displacement platform, the distance measuring bar being configured to measure a distance between the distance measuring bar and the base and to return the distance to the piezoceramic displacement platform so as to adjust a distance between the upper sample assembly and the lower sample assembly.

According to an embodiment of the present disclosure, the high-speed rheometer further includes: an eddy current sensor disposed on the base and below the distance measuring bar, the distance measuring bar being further configured to measure a distance between the distance measuring bar and the eddy current sensor; and a sensor carrier disposed on the base, the eddy current sensor being disposed on the sensor carrier.

According to an embodiment of the present disclosure, the high-speed rheometer further includes a connecting bar via which the torsion bar and the piezoceramic displacement platform are connected with each other.

According to an embodiment of the present disclosure, the upper sample assembly includes: an upper sample having an upper surface and a lower surface contacted with the fluid to be tested; and an upper sample connector defining two ends connected with the upper surface of the upper sample and a lower surface of the torsion bar respectively.

According to an embodiment of the present disclosure, the lower sample assembly includes: a lower sample connector disposed on the driving device; and a lower sample disposed on the lower sample connector, the fluid to be tested being disposed on an upper surface of the lower sample.

According to an embodiment of the present disclosure, two spaced supporting pillars are disposed on the upper surface of the lower sample connector and extend upwards from the upper surface of the lower sample connector, and a supporting platform having a spherical upper surface is disposed between the two supporting pillars; two mounting grooves are disposed in the lower surface of the lower sample and configured to cooperate with the two supporting pillars respectively, and the lower surface of the lower sample abuts against the upper surface of the supporting platform.

According to an embodiment of the present disclosure, the lower sample is fixedly connected with the lower sample connector, and the upper sample assembly includes: an upper sample connector connected with the lower surface of the torsion bar, two spaced supporting bars being disposed on the lower surface of the upper sample connector and extend downwards from the lower surface of the upper sample connector, a supporting ball having a spherical lower surface being disposed between the two supporting bars; and an upper sample having two connecting grooves in an upper surface thereof and configured to cooperate with the two connecting bars respectively, a receiving groove being provided between the two connecting grooves and configured to cooperate with the supporting ball, the two supporting bars being inserted in the two connecting grooves respectively and the supporting ball being received in the receiving groove, the upper sample being connected with the upper sample connector if the lower surface of the upper sample is flush with the upper surface of the lower sample.

According to an embodiment of the present disclosure, the upper sample is fixedly connected with the upper sample connector via a binder.

According to an embodiment of the present disclosure, the binder includes glue.

According to an embodiment of the present disclosure, a process of assembling the upper sample and the upper sample connector includes: attaching the lower surface of the upper sample to the upper surface of the lower sample, such that the lower surface of the upper sample is parallel to the upper surface of the lower sample; contacting the upper sample connector with the upper sample, such that the supporting bars are inserted in the connecting grooves respectively and the supporting ball is received in the receiving groove; and fixedly connecting the upper sample to the upper sample connector, and moving the upper sample connector upwards to remove the upper sample from the lower sample.

Additional aspects and advantages of embodiments of present disclosure will be given in part in the following descriptions, become apparent in part from the following descriptions, or be learned from the practice of the embodiments of the present disclosure.

BRIEF DESCRIPTION OF THE DRAWINGS

These and other aspects and advantages of embodiments of the present disclosure will become apparent and more readily appreciated from the following descriptions made with reference to the accompanying drawings, in which.

DETAILED DESCRIPTION

Figure 1:
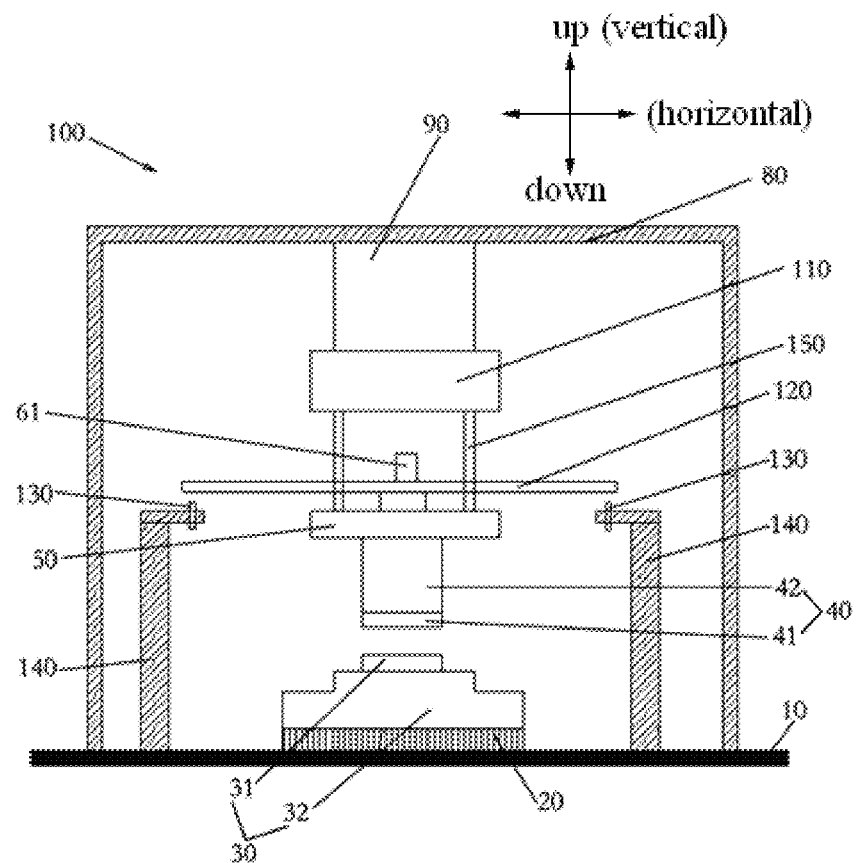
FIG. 1 is a structural schematic diagram of a high-speed rheometer according to an embodiment of the present disclosure.

Reference will be made in detail to embodiments of the present disclosure. The embodiments described herein with reference to drawings are explanatory, illustrative, and used to generally understand the present disclosure. The embodiments shall not be construed to limit the present disclosure. The same or similar elements and the elements having same or similar functions are denoted by like reference numerals throughout the descriptions.

A high-speed rheometer according to embodiments of the present disclosure will be described below with reference to the drawings. In embodiments of the present disclosure, "high-speed" may indicate a shearing rate ranging from 1/s to $1 \times 10^6$/s.

As shown in FIGS. 1-5, according to an embodiment of the present disclosure, a high-speed rheometer 100 includes a base 10, a driving device 20, a lower sample assembly 30, an upper sample assembly 40, a torsion bar 50 and an optical torque measuring assembly. The driving device 20 is disposed on the base 10, the lower sample assembly 30 is connected with the driving device 20 and is rotatable along an axial direction thereof (for example, up-down direction) under the driving of the driving device 20. The fluid to be tested (not shown) is disposed on the lower sample assembly 30. The upper sample assembly 40 is disposed above the lower sample assembly 30, configured to contact with the fluid to be tested, and is rotatable along the axial direction under the driving of the fluid to be tested. The torsion bar 50 is disposed on the upper sample assembly 40 and torsional upon the rotation of the upper sample assembly 40. The optical torque measuring assembly is configured to measure a torsion angle of the torsion bar 50 so as to obtain a torque generated during shearing the fluid to be tested.

With the high-speed rheometer 100 according to embodiments of the present embodiment, the driving device 20 drives the lower sample assembly 30 and the fluid to be tested to rotate, and the upper sample assembly 40 contacted with the fluid to be tested rotates accordingly. Therefore, the torsion bar 50 connected with the upper sample assembly 40 is driven to twist, and the optical torque measuring assembly may measure the torsion angle of the torsion bar 50, so as to obtain the torque generated by the fluid to be tested. A fact that the torque of the fluid to be tested is measured by using an optical measuring method not only improves the measuring accuracy of the high-speed rheometer, but also broadens the measuring range or measuring span. Specifically, the measuring range of the shearing rate may be increased by several orders of magnitude, which may cover both the low rate area and the high rate area.

During operation of the high-speed rheometer 100 according to embodiment of the present disclosure, the fluid to be tested is disposed on the lower sample assembly 30 and the upper sample assembly 40 is contacted with the fluid to be tested. The driving device 20 drives the upper sample assembly 40 to rotate axially (i.e. about the axial direction). Because the fluid to be tested has certain viscosity, it may drive the upper sample assembly 40 to twist or deflect. As the torsion bar 50 is connected with the upper sample assembly 40, the torsion bar 50 may twist or deflect by a corresponding angle accordingly. The optical torque measuring assembly can measure the torsion angle of the torsion bar 50, and then the shearing torque of the fluid to be tested may be obtained according to the torsion angle.

The optical measuring method has high accuracy and fast response. Even if the torsion bar 50 slightly twists by a small angle, the optical torque measuring assembly may sense the torsion and measure the torsion angle quickly, which improves both the measuring accuracy and the resolution of the high-speed rheometer 100. In addition, if the torsion bar 50 twists by a relatively larger angle, the optical torque measuring assembly may also sense the torsion and measure the torsion angle accordingly. With the high-speed rheometer 100 according to embodiments of the present disclosure, an optical torque measuring assembly is contained in the high-speed rheometer 100, which not only improves the measuring accuracy but also the responding speed of the high-speed rheometer 100. Further, measurements with in a relatively larger range may be achieved, and thus the high-speed rheometer 100 may be suitable for measuring rheological behaviors of various different fluids, and the measuring span of the high-speed rheometer 100 is increased.

In an embodiment of the present disclosure, the optical torque measuring assembly includes a prism 61, a light source 62 and a four-quadrant detector 63. The prism 61 is disposed on the torsion bar 50 and is coaxial with the torsion bar 50. The light source 62 is configured to emit light towards a side surface of the prism 61 to form first reflected light. The four-quadrant detector 63 receives the first reflected light from the prism 61.

Specifically, the base 10 is horizontally arranged. The driving device 20 is disposed on an upper surface of the base 10, the lower sample assembly 30 is disposed above the driving device 20, and the fluid to be tested may be contained on an upper surface of the lower sample assembly 30. The upper sample assembly 40 is disposed above the lower sample assembly 30, and an upper part of the upper sample assembly 40 is connected with the torsion bar 50. The prism 61 is connected with an upper part of the torsion bar 50, while a reflecting surface of the prism 61 is vertical to the horizontal plane. A lower surface of the upper sample assembly 40 is contacted with the fluid to be tested, and the lower surface of the upper sample assembly 40 and the lower sample assembly 30 is flush with and opposite to each other.

The prism 61 is connected with the torsion bar 50 and is coaxial with the torsion bar 50, and the prism 61 can deflect together with the torsion bar 50. The light emitted by the light source 62 arrives horizontally at a reflecting surface of the prism 61, and light reflected by the prism 61 arrives directly at a detecting surface of the four-quadrant detector 63. During operation of the high-speed rheometer 100, the torsion bar 50 rotates axially, which causes the light reflected by the prism 61 to deflect. Thus, a light spot or light point of the light reflected by the prism 61 on the detecting surface of the four-quadrant detector 63 moves, and the four-quadrant detector 63 may output a voltage value.

Thereby, the optical torque measuring assembly may convert the torque of the fluid to be tested into the axial deflection of the torsion bar 50 and the prism 61, the light reflected by the prism 61 deflects, and the light spot or light point thereof on the detecting surface of the four-quadrant detector 63 moves, and the movement of the light spot or light point is converted into the voltage value of the four-quadrant detector 63. The torque of the fluid to be tested can be obtained according to the voltage value.

There are not particular limits to the light source 62. Alternatively, the light source 62 may be a laser which has excellent monochromaticity, directivity, and high luminance. With the laser as the light source, the light source 62 may produce a straight light path, thus facilitating to increase the measuring accuracy of the optical torque measuring assembly.

There are no particular limits to the driving device 20 either, provided it is capable of driving the lower sample assembly 30 to rotate axially. Alternatively, the driving device 20 may be an air float spindle drive system which includes an air float spindle motor and a controller. The air float spindle motor has low wear and resistance, and high accuracy, especially particularly high axial rotation accuracy and radial rotation accuracy. In addition, the air float spindle motor can provide high rotating speed and have relatively smaller power loss. With the air float spindle drive system, the measuring accuracy of the high-speed rheometer 100 can be further increased. Specifically, the driving device 20 can control the rotating speed of the air float spindle motor via a controller, which ensures that the fluid to be tested can rotate stably at a preset shearing rate.

In an embodiment of the present disclosure, the optical torque measuring assembly further includes at least one reflector. The reflector reflects the light reflected by the prism 61 to form second reflected light, and sends the second reflected light to the four-quadrant detector 63. Specifically, first the prism 61 reflects light from the light source, and then the reflector reflects the light reflected by the prism 61 to the four-quadrant detector 63. In this way, with the reflector, the light path from the prism 61 to the four-quadrant detector 63 becomes an angled line other than being straight. Thereby, with the high-speed rheometer 100 according to embodiments of the present disclosure, the light from the prism 61 to the four-quadrant detector 63 is further reflected by the reflector and the light path becomes angled, without shortening the length of the light path. In this way, a condition that a dimension of the base 10 is too long in a certain direction may be avoided, which provides the base 10 with a more reasonable size.

According to an embodiment of the present disclosure, the four-quadrant detector 63 defined a predetermined position thereon. The predetermined position is defined as a position on the four-quadrant detector 63 at which the light reflected by the prism 61 arrive if the prism 61 does not twist. The optical torque measuring assembly further includes a feedback circuit (not shown) and a piezoceramic deflection platform 64. The four-quadrant detector 63 receives the reflected lights from the prism 61 before and after rotation of the prism 61 and generates a voltage difference, and the feedback circuit amplifies the voltage difference to obtain an amplifying signal. The piezoceramic deflection platform 64 is disposed on the at least one reflector, receives the amplifying signal and drives the reflector to deflect, such that the light reflected by the reflector will arrive at the predetermined position.

It is to be understood that, there are no particular limits to the number of the reflectors, which may be arranged according to practical requirements. Alternatively, in an embodiment of the present disclosure, the at least one reflector includes sequentially disposed first to fourth reflectors 71, 72, 73, 74, and the piezoceramic deflection platform 64 is disposed on the first reflector 71.

Figure 2:
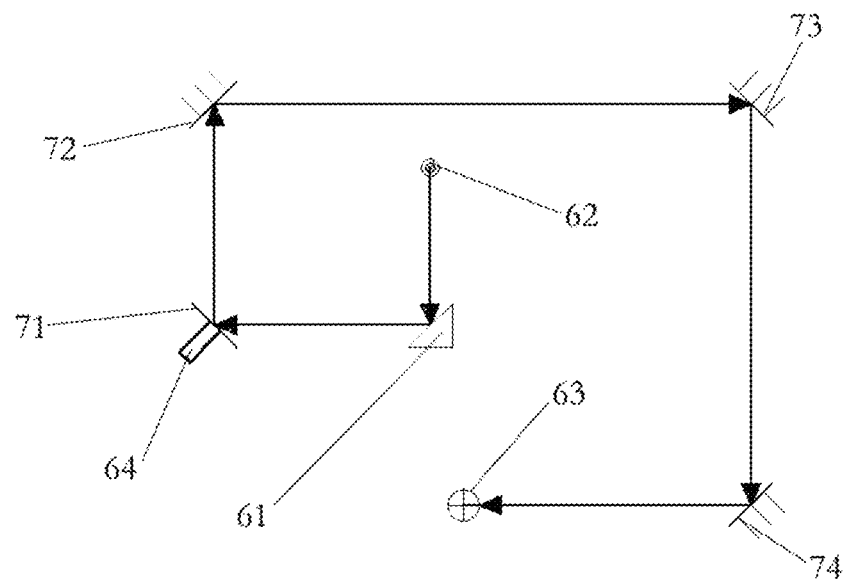
FIG. 2 is a schematic diagram showing light paths of a high-speed rheometer according to an embodiment of the present disclosure.

Specifically, the light source 62 and the first to fourth reflectors 71, 72, 73, 74 are all vertically fixed above the base 10. As shown in FIG. 2, the light source 62 emits a horizontal light beam, and the light beam arrives at the detecting surface of the four-quadrant detector 63 after being reflected by the prism 61, and the first to fourth reflectors 71, 72, 73, 74.

If the light path is deflected, the light spot or light point on the detecting surface of the four-quadrant detector 63 may move, and the four-quadrant detector 63 may generate a voltage value. The feedback circuit amplifies the voltage value and sends the amplified voltage value to the piezoceramic deflection platform 64 fixed on the first reflector 71. Under the control of a negative feedback circuit, the piezoceramic deflection platform 64 deflects by a corresponding angle, which drives the first reflector 71 connected with the piezoceramic deflection platform 64 to deflect by a corresponding angle accordingly, such that the light spot or light point of the light arrive at the predetermined position on the four-quadrant detector 63.

If the rotating speed of the driving device 20 is relatively lower, the shearing torque of the fluid to be tested is relatively smaller, and the torsion angles of the torsion bar 50 and the prism 61 are relatively smaller. In this condition, even though the light emitted by the light source 62 may be deflected by the prism 61 and the at least one reflectors, the light spot or light point of the light on the four-quadrant detector 63 may not move out of the detecting surface of the four-quadrant detector 63.

If the rotating speed of the driving device 20 is relatively higher, the shearing torque of the fluid to be tested is relatively larger, and the torsion angles of the torsion bar 50 and the prism 61 are relatively larger. In this condition, the light spot or light point of the light on the four-quadrant detector 63 tends to move out of the detecting surface of the four-quadrant detector 63. Then the negative feedback circuit may control the first reflector 71 to deflect by a certain angle according to the voltage output by the four-quadrant detector 63, so that the light spot or light point of the light on the four-quadrant detector 63 may move to the predetermined position in the detecting surface of the four-quadrant detector 63.

The voltage value output by the four-quadrant detector 63 is in proportion to the deflection angle of the light. In other words, the larger the shearing torque of the fluid to be tested is, the larger the voltage value output by the four-quadrant detector 63 is.

Thereby, the torque of the fluid to be tested can be obtained according to the voltage value output by the four-quadrant detector 63. In the case that the torque of the fluid to be tested is relatively larger, the high-speed rheometer 100 can measure the torque of the fluid to be tested. Therefore, the high-speed rheometer 100 can not only measure fluids at relatively lower shearing rate, but also can measure fluids at relatively higher shearing rate, i.e. the high-speed rheometer 100 has a large measuring range or measuring span.

There are no particular limits to the incidence angle of the light arriving at the reflector and the reflection angle of the light leaving the reflector, provided the at least one reflector is reasonably arranged above the base 10 and reflects the lights emitted by the light source 62. For example, the angle between the incidence light and the reflecting light of the reflector may be an obtuse angle or a right angle. Alternatively, as shown in FIG. 2, in a specific embodiment of the present disclosure, the angle between the incidence light and the reflecting light of each of the first to fourth reflectors 71, 72, 73, 74 is a right angle, and the angle between the incidence light and the reflecting light of the prism 61 is also a right angle. This arrangement facilitates to mount and arrange other components on the base 10 and to control the direction of lights.

It is to be understood that, the location of the piezoceramic deflection platform 64 is not limited to the first reflector. For example, the piezoceramic deflection platform 64 may be disposed on one or more of the prism 61, the second reflector 72, the third reflector 73 and the fourth reflector 74. At these locations, the piezoceramic deflection platform 64 can also deflect a corresponding angle in relative to the reflector or prism 61 connected with the piezoceramic deflection platform 64 itself according to the voltage value output by the four-quadrant detector 63, so that the light spot or light point arrive at the predetermined position of the detecting surface of the four-quadrant detector 63.

According to an embodiment of the present disclosure, the high-speed rheometer 100 further includes an upper sample carrier 80 and a manual displacement platform 90. The upper sample carrier 80 is disposed on the base 10, and the manual displacement platform 90 is disposed on the upper sample carrier 80 and connected with the upper sample assembly 40 so as to adjust the position of the upper sample assembly 40 in the up-down direction. Specifically, the manual displacement platform 90 has a long displacement route and a low resolution, which may be used to control movements having a long movement route. Thus, the manual displacement platform 90 can move the upper sample assembly 40 upwards and downwards to replace the fluid to be tested, thus being capable of measuring fluids of various different kinds.

Further, according to embodiments of the present disclosure, the high-speed rheometer 100 further includes a piezoceramic displacement platform 110 and a distance measuring bar 120. The piezoceramic displacement platform 110 is disposed below the manual displacement platform 90 and connected with the manual displacement platform 90. The distance measuring bar 120 is arranged in the horizontal direction on the torsion bar 50 and connected with the piezoceramic displacement platform 110. The distance measuring bar 120 can measure a distance between the distance measuring bar 120 and the base 10 and feedback the distance to the piezoceramic displacement platform 110, and the piezoceramic displacement platform 110 adjusts the distance between the lower sample assembly 30 and the upper sample assembly 40 accordingly.

Specifically, the upper sample carrier 80 having a substantial inverted U-shape is disposed above the base 10. The manual displacement platform 90 is connected with a lower part of the upper sample carrier 80, and the piezoceramic displacement platform 110 and the torsion bar 50 are connected with a lower part of the manual displacement platform 90 sequentially. The distance measuring bar 120 is fixed below the prism 60 and above the torsion bar 50. In other words, the prism 61 is fixed above the distance measuring bar 120.

Further, the piezoceramic displacement platform 110 has a relatively higher resolution which may be as high as nanoscale. Thereby, the piezoceramic displacement platform 110 has a short displacement route and high resolution, which may be used to precisely control the distance between the lower sample assembly 30 and the upper sample assembly 40.

In a specific embodiment of the present disclosure, the high-speed rheometer 100 further includes an eddy current sensor 130 and a sensor support 140. The eddy current sensor 130 is disposed on the base 10 and below the distance measuring bar 120, and the distance measuring bar 120 can further measure the distance between the distance measuring bar 120 and the eddy current sensor 130. The sensor support 140 is disposed on the base 10, and the eddy current sensor 130 is disposed on the sensor support 140.

Specifically, two ends of the distance measuring bar 120 in the horizontal direction are suspended, and two eddy current sensors 130 are disposed below two ends of the distance measuring bar 120 respectively. Accordingly, two sensor supports 140 are provided to fix the two eddy current sensors 130 respectively, and the two eddy current sensors 130 are located in a same horizontal plane.

In addition, the eddy current sensor 130 is a non-contact element having a large measuring range and high sensitivity, which can perform axial displacement and radial displacement and measure parameters such as rotating speed or phase position. As the distance measuring bar 120 is connected with the upper sample assembly 40, the height of the distance measuring bar 120 may change if the height of the upper sample assembly 40 changes in the up-down direction. In this way, the eddy current sensor 130 may obtain position information of the upper sample assembly 40 by sensing the position information of the distance measuring bar 120, and thus the eddy current sensor 130 can precisely measure the distance between the upper sample assembly 40 and the lower sample assembly 30.

Thereby, the piezoceramic displacement platform 110 may be used to adjust the displacement of the upper sample assembly 40 at a nanoscale level, the eddy current sensor 130 may be used to precisely measure the height of the upper sample assembly 40 in the up-down direction, and the piezoceramic displacement platform 110 cooperates with the eddy current sensor 130 to adjust the distance between the upper sample assembly 40 and lower sample assembly 30, thereby providing a high accuracy for controlling the position of the upper sample assembly 40.

It is to be understood that, the eddy current sensor 130 of the high-speed rheometer 100 according to embodiments of the present disclosure may be of other type, provided the eddy current sensor 130 has relatively higher resolution.

According to embodiments of the present disclosure, the high-speed rheometer 100 further includes a connecting bar 150. The torsion bar 50 and the piezoceramic displacement platform 110 and connected with each other via the connecting bar 150.

Specifically, an end of the connecting bar 150 is connected with the piezoceramic displacement platform 110, and the other end of the connecting bar 150 is connected with the torsion bar 50. In order to fasten the connection between the piezoceramic displacement platform 110 and the torsion bar 50, a plurality of connecting bars 150 may be provided to connect the piezoceramic displacement platform 110 with the torsion bar 50. Thereby, the manual displacement platform 90 and/or the piezoceramic displacement platform 110 may adjust the distance between the upper sample assembly 40 and the lower sample assembly 30 via the connecting bar 150.

Figure 3:
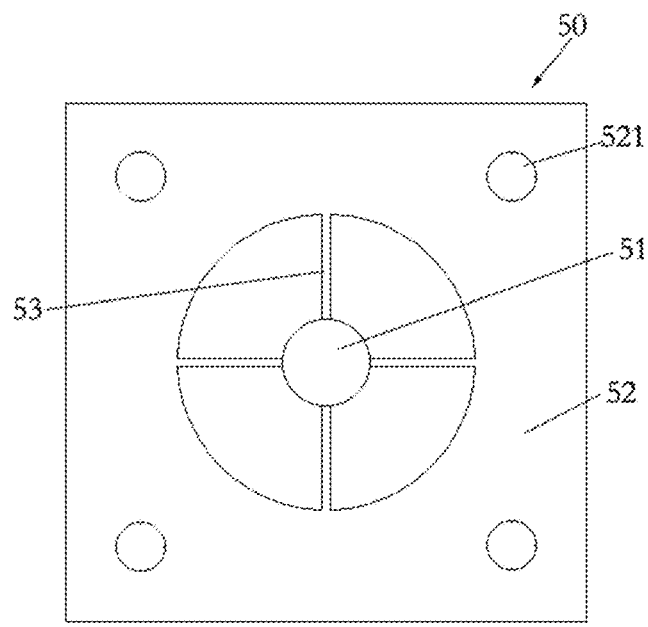
FIG. 3 is a structural schematic diagram of a torsion bar a high-speed rheometer according to an embodiment of the present disclosure.

Alternatively, as shown in FIG. 3, in an embodiment of the present disclosure, the torsion bar 50 includes a first fixing part 51, a second fixing part 52 and a bar part 53. Specifically, the first fixing part 51 locates in the center of the torsion bar 50, a lower part of the first fixing part 51 is connected with the upper sample assembly 40, and an upper part of the first fixing part 51 is connected with the distance measuring bar 120 and the prism 61 respectively. The second fixing part 52 is disposed at the outer periphery of the first fixing part 51 and connected with the connecting bar 150. A plurality of bar parts 53 are provided and disposed uniformly along the periphery of the first fixing part 51, each of the bar part 53 is connected with the first and second fixing parts 51, 52.

It is to be understood that, there is no particular limits to the shape of the torsion bar 50. Alternatively, the first fixing part 51 has a substantial circular cross section. The second fixing part 52 has ring-like cross section, while the outer periphery of the cross section of the second fixing part 52 is substantial rectangular, while the inner periphery of the cross section of the second fixing part 52 is substantial circular. Four bar parts 53 are provided, and each of the bar parts 53 is connected with the outer periphery of the first fixing part 51 and the inner periphery of the second fixing part 52. Each of the four corners of the second fixing part 52 is provided with a connecting hole 521 configured to connect with the connecting bar 150.

If the upper sample system 40 twists axially, the first fixing part 51 connected with the upper sample system 40 will be driven by a torque generated by the upper sample system 40. As the bar part 53 is a elongated bar which tends to deform upon an external force, the bar part 53 connected with the first fixing part 51 will bend about the center of the torsion bar 50 and the first fixing part 51 connected with the bar part 53 will twist axially, which drives the prism 61 to twist accordingly. While the second fixing part 52 is connected with the connecting bar 150, so the second fixing part 52 hardly twist.

Alternatively, according to an embodiment of the present embodiment, the upper sample system 40 includes an upper sample 41 and an upper sample connector 42. A lower surface of the upper sample 41 is to be contacted with the fluid to be tested, and the upper sample connector 42 is connected with an upper surface of the upper sample 41 and the lower surface of the torsion bar 50 respectively.

Accordingly, according to an embodiment of the present embodiment, the lower sample system 30 includes a lower sample connector 32 and a lower sample 31. The lower sample connector 32 is disposed on the driving device 20, the lower sample 31 is disposed on the lower sample connector 32, and the fluid to be tested is disposed on the upper surface of the lower sample 31.

Figure 4:
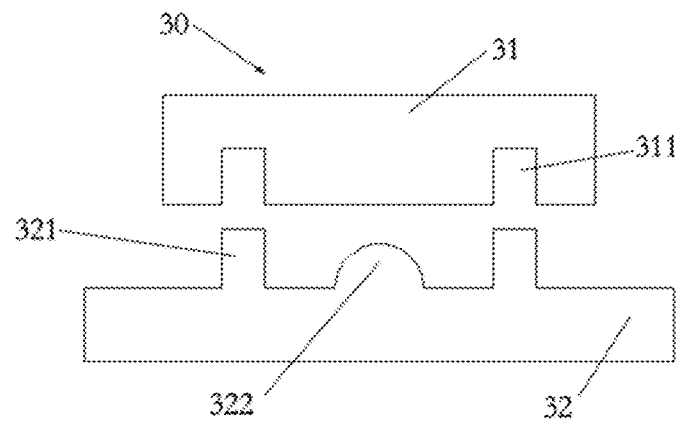
FIG. 4 is a perspective diagram of a lower sample assembly of a high-speed rheometer according to an embodiment of the present disclosure.
Figure 5:
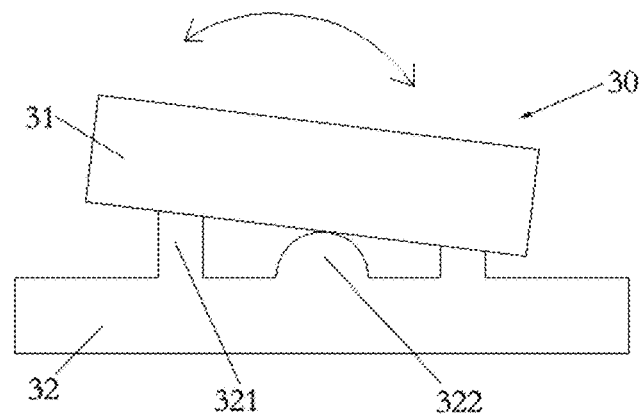
FIG. 5 is a schematic diagram showing an operating principle of a lower sample assembly of a high-speed rheometer according to an embodiment of the present disclosure.

As shown in FIGS. 4 and 5, in an embodiment of the present disclosure, two supporting pillars 321 are disposed on the upper surface of the lower sample connector 32, the two supporting pillars 321 are spaced apart from each other and extending upwards from the surface of the lower sample connector 32. A supporting platform 322 having a spherical upper surface is disposed between the two supporting pillars 321, and two amounting grooves 311 cooperated with the two supporting pillars 321 accordingly are formed in the lower surface of the lower sample 31. The lower surface of the lower sample 31 abuts against the upper surface of the supporting platform 322.

Specifically, the lower sample 31 and the lower sample connector 32 form a flexible connection. As the two supporting pillars 321 of the lower sample connector 32 are inserted into the two mounting grooves 311 of the lower sample 31, torques may be transmitted between the lower sample connector 32 and the lower sample via the supporting pillars 321 and the mounting grooves 311. As shown in FIGS. 4 and 5, the upper surface of the supporting platform 322 of the lower sample connector abuts against the lower surface of the lower sample 31, the lower sample connector 32 and the lower sample 31 form a hemispherical automatic leveling mechanism, and arrows in FIG. 5 show a movement of the lower sample 31 on the lower sample connector 32. During rotation, the lower sample 31 may rotate and sway freely on the supporting platform 322. The lower sample 31 and the upper sample 41 may be maintained to be parallel to each other by adjusting the rotation of the lower sample 31.

It is to be noted that, the diameter of the mounting groove 311 is larger than that of the supporting pillar 321, and the mounting groove 311 may be fitted over the supporting pillar 321. During rotation or swing of the lower sample 31 on the lower sample connector 32, the mounting groove 311 and the supporting pillar may not interfere with each other, which further improves the automatic leveling performances between the lower sample 31 and the lower ample connector 32.

Figure 6:
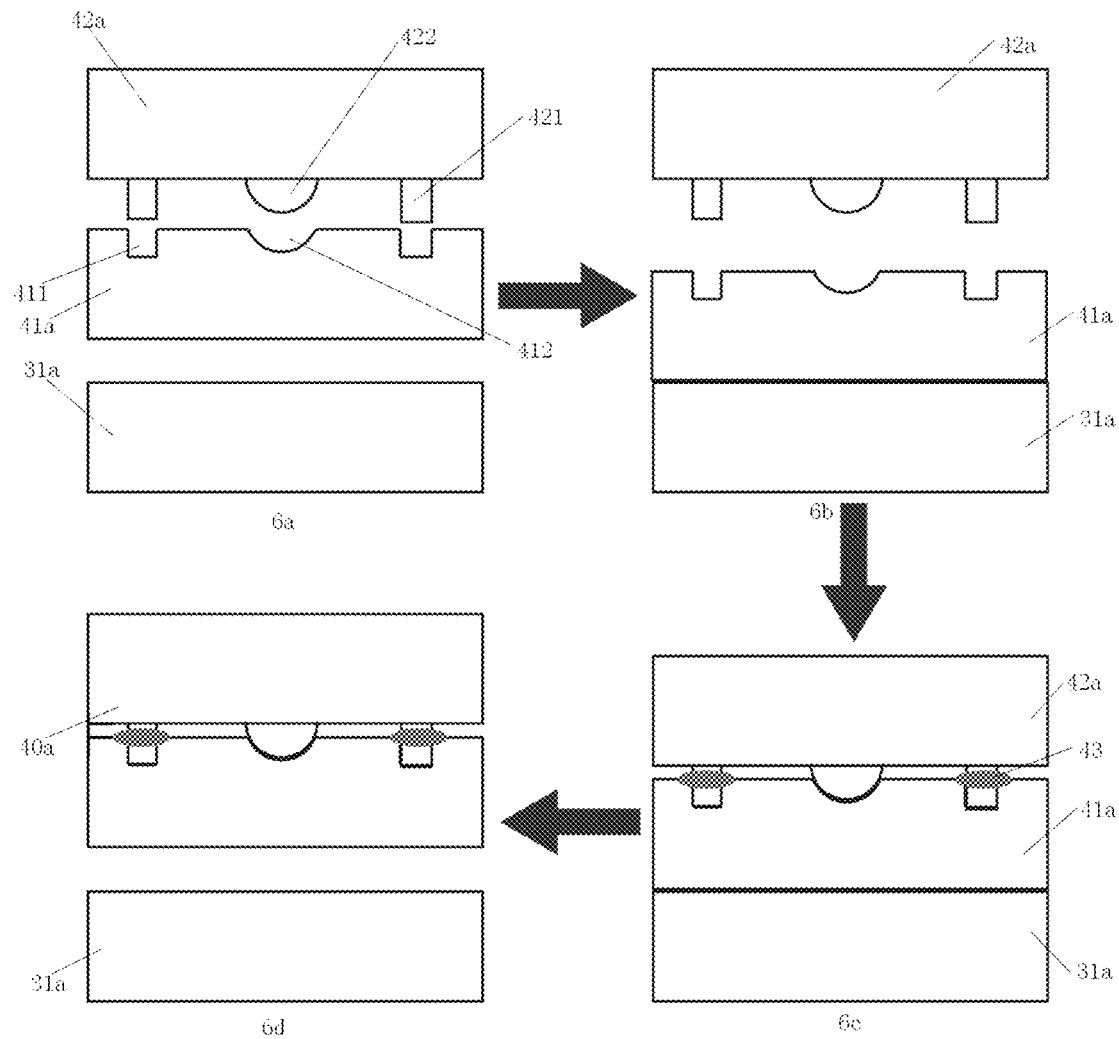
FIG. 6 is a flow chart showing a process of preparing a lower sample assembly of a high-speed rheometer according to an embodiment of the present disclosure.

As shown in FIG. 6, in some embodiments of the present disclosure, the lower sample 31*a* is fixedly connected with the lower sample connector, and the upper sample system 40*a* includes an upper sample connector 42*a* and an upper sample 41*a*.

Specifically, the upper sample connector 42*a* is connected with a lower surface of the torsion bar. Two supporting bars 421 are disposed on the lower surface of the upper sample connector 42*a*, the two supporting bars 421 are spaced apart from each other and extend downwards from the surface of the upper sample connector 42*a*. A supporting ball 422 having a spherical lower surface is disposed between the two supporting bars 421. Two connecting grooves 411 configured to cooperate with the two supporting bars 421 are formed in the upper surface of the upper sample 41*a*. A receiving groove 412 configured to cooperate with the supporting ball 422 is disposed between the two connecting grooves 411. The two supporting bars 421 are inserted into the two connecting grooves 411 respectively, and the supporting ball 422 is received in the receiving groove 412. The upper sample 41*a* may connect with the upper sample connector 42*a* if the lower surface of the upper sample 41*a* is flush with the upper surface of the lower sample 31*a*.

A process of assembling the upper sample 41*a* and the upper sample connector 42*a* may specifically include following steps.

Firstly, the lower surface of the upper sample 41*a* is attached with the upper surface of the lower sample 31*a*, so that the lower surface of the upper sample 41*a* is parallel with the upper surface of the lower sample 31*a* (as shown in FIG. 6*b*).

Subsequently, the upper sample connector 42*a* is contacted with the upper sample 41*a*, and the supporting bars 421 are inserted into the connecting grooves 411 respectively and the supporting ball 422 is received in the receiving groove 412 (as shown in FIG. 6*c*).

Then the upper sample 41*a* is fixedly connected with the upper sample connector 42*a*, and specifically the upper sample 41*a* and the upper sample connector 42*a* are boned together with glue (as shown in FIG. 6*c*). Finally, the upper sample connector 42*a* is moved upwards, so that the upper sample 41*a* is removed from the lower sample 31*a*, which ensures the upper sample 41*a* is parallel to the lower sample 31*a* (as shown in FIG. 6*d*).

In a specific embodiment of the present disclosure, the upper sample 41*a* and the upper sample connector 42*a* are fixedly connected with each other via a binder 43, and the binder 43 may be glue.

In other words, in this embodiment, firstly the upper sample 41*a* is contacted with the lower sample 31*a*, and the upper sample 41*a* and the lower sample 31*a* are parallel to each other due to gravity. Then the upper sample connector 42*a* is moved downwards to contact with the upper sample 41*a*, and then glue is provided between the upper sample 41*a* and the upper sample connector 42*a*. After solidification of the glue, the upper sample 41*a* is moved upwards, thus ensuring that the upper sample 41*a* is parallel to the lower sample 31*a*.

An operating principle of the high-speed rheometer 100 according to embodiments of the present disclosure will be described below in detail.

As shown in FIG. 2, after being reflected by the prism 61 and the first to fourth reflectors 71, 72, 73, 74 sequentially, light emitted by the light source 62 finally arrives at the four-quadrant detector 63. When the high-speed rheometer 100 is operating, the driving device 20 drives the lower sample system 30 and the fluid to be tested rotate. The upper sample system 40 is contacted with the fluid to be tested, and the torsion bar 50 connected with the upper sample system 40 deforms and twists. If the first fixing part 51 rotates by an angle, the prism 61 connected with the first fixing part 51 twists by a corresponding angle, and thus the light spot or light point illuminated on the four-quadrant detector 63 moves accordingly.

Then the four-quadrant detector 63 may output a voltage value. The feedback circuit amplifies the voltage value and sends the amplified voltage value to the piezoceramic deflection platform 64, and the piezoceramic deflection platform 64 deflects by a corresponding angle, which forms a negative feedback with the four-quadrant detector 63. In this way, the light finally illuminates on the predetermined position of the four-quadrant detector 63. The voltage value output by the four-quadrant detector 63 is in proportion to the deflection angle of the light, and thus the torque of the fluid to be tested may be obtained according to the voltage value output by the four-quadrant detector 63.

In a word, the high-speed rheometer 100 according to embodiments of the present disclosure uses an optical torque measuring system to measure the torque of the fluid to be tested, which not only improves the measuring accuracy, but also improves the measuring range. Specifically, the measuring range for shearing rate is increased by several orders of magnitude, and the measuring range for rheological behaviors covers for both low rate area and high rate area. The piezoceramic displacement platform 110 and the eddy current sensor 130 are used to control displacements, in which the piezoceramic displacement platform 110 is used to generate a nanoscale displacement, and the eddy current sensor 130 detects the displacement. With the combination of the piezoceramic displacement platform 110 and the eddy current sensor 130, relatively higher position control accuracy can be achieved. The high-speed rheometer 100 has relatively broader and accurate measuring range, and thus is suitable for measuring rheological behaviors of various different fluids.

In the specification, it should be understood that, the terms such as "central", "longitudinal", "lateral", "width", "thickness", "above", "below", "front", "rear", "right", "left", "vertical", "horizontal", "top", "bottom", "inner", "outer", "clockwise", "counter-clockwise" should be construed to refer to the orientation as then described or as shown in the drawings. These terms are merely for convenience and concision of description and do not alone indicate or imply that the device or element referred to must have a particular orientation. Thus, it cannot be understood to limit the present disclosure.

In addition, terms such as "first" and "second" are used herein for purposes of description and are not intended to indicate or imply relative importance or significance or impliedly indicate quantity of the technical feature referred to. Thus, the feature defined with "first" and "second" may comprise one or more this feature. In the description of the present disclosure, "a plurality of" means two or more than two this features, unless specified otherwise.

In the present invention, unless specified or limited otherwise, the terms "mounted," "connected," "coupled," "fixed" and the like are used broadly, and may be, for example, fixed connections, detachable connections, or integral connections; may also be mechanical or electrical connections; may also be direct connections or indirect connections via intervening structures; may also be inner communications of two elements, which can be understood by those skilled in the art according to specific situations.

Reference throughout this specification to "an embodiment," "some embodiments," "one embodiment", "another example," "an example," "a specific example," or "some examples," means that a particular feature, structure, material, or characteristic described in connection with the embodiment or example is included in at least one embodiment or example of the present disclosure. Thus, the appearances of the phrases such as "in some embodiments," "in one embodiment", "in an embodiment", "in another example," "in an example," "in a specific example," or "in some examples," in various places throughout this specification are not necessarily referring to the same embodiment or example of the present disclosure. Furthermore, the particular features, structures, materials, or characteristics may be combined in any suitable manner in one or more embodiments or examples.

Although explanatory embodiments have been shown and described, it would be appreciated by those skilled in the art that the above embodiments can not be construed to limit the present disclosure, and changes, alternatives, and modifications can be made in the embodiments without departing from spirit, principles and scope of the present disclosure.

What is claimed is:

1. A rheometer comprising:
a base;
a driving device disposed on the base;
a lower sample assembly connected with the driving device and being rotatable under the driving of the driving device, fluid to be tested being disposed on the lower sample assembly;
an upper sample assembly disposed above the lower sample assembly and adapted to contact with the fluid to be tested, the upper sample assembly being rotatable under the driving of the fluid;
a torsion bar disposed on the upper sample assembly and being torsional upon the rotation of the upper sample assembly; and
an optical torque measuring assembly configured to measure a torsion angle of the torsion bar so as to obtain a torque generated during shearing the fluid to be tested;
wherein the optical torque measuring assembly comprises:
a prism coaxially disposed on the torsion bar;
a light source configured to emit light toward a side surface of the prism to form first reflected light; and
a four-quadrant detector configured to receive the first reflected light.

2. The rheometer of claim 1, wherein the optical torque measuring assembly further comprises at least one reflector configured to receive the first reflected light, to generate second reflected light and to send the second reflected light to the four-quadrant detector.

3. The rheometer of claim 2, wherein the four-quadrant detector has a predetermined position at which the first reflected light and the second reflected light arrive when the prism is not twisted, the four-quadrant detector is further configured to receive reflected lights from the prism before and after rotation of the prism and to generate a voltage difference, and the optical torque measuring assembly further comprises:
a feedback circuit configured to amplify the voltage difference to obtain an amplifying signal; and
a piezoceramic deflection platform disposed on the at least one reflector and configured to receive the amplifying signal and to drive the reflector to deflect, such that the reflected light from the reflector arrives at the predetermined position.

4. The rheometer of claim 3, wherein the at least one reflector comprises first to fourth reflectors, and the piezoceramic deflection platform is disposed on the first reflector.

5. The rheometer of claim 1, further comprising:
an upper sample carrier disposed on the base;
a manual displacement platform disposed on the upper sample carrier and connected with the upper sample assembly, the manual displacement platform being configured to adjust position of the upper sample assembly in an upper-down direction;
a piezoceramic displacement platform disposed below and connected with the manual displacement platform;
a distance measuring bar disposed on the torsion bar along a horizontal direction and connected with the piezoceramic displacement platform, the distance measuring bar being configured to measure a distance between the distance measuring bar and the base and to return the distance to the piezoceramic displacement platform so as to adjust a distance between the upper sample assembly and the lower sample assembly; and a connecting bar via which the torsion bar and the piezoceramic displacement platform are connected with each other, wherein the torsion bar comprises:
a first fixing part located in the center of the torsion bar and having a lower part connected with the upper sample assembly and an upper part connected with the distance measuring bar and the prism respectively;

a second fixing part disposed at an outer periphery of the first fixing part and connected with the connecting bar; and a plurality of bar parts provided and disposed uniformly along a periphery of the first fixing part, each of the plurality of bar parts being connected with the first fixing part and the second fixing part.

6. The rheometer of claim 5, wherein the first fixing part has a substantial circular cross section, the second fixing part has a ring-like cross section, an outer periphery of the cross section of the second fixing part is substantial rectangular, and an inner periphery of the cross section of the second fixing part is substantial circular.

7. The rheometer of claim 6, wherein four bar parts are provided, and each of the four bar parts is connected with the outer periphery of the first fixing part and an inner periphery of the second fixing part.

8. The rheometer of claim 7, wherein each of four corners of the second fixing part is provided with a connecting hole configured to connect with the connecting bar.

9. A rheometer, comprising:
a base;
a driving device disposed on the base;
a lower sample assembly connected with the driving device and being rotatable under the driving of the driving device, fluid to be tested being disposed on the lower sample assembly;
an upper sample assembly disposed above the lower sample assembly and adapted to contact with the fluid to be tested, the upper sample assembly being rotatable under the driving of the fluid;
a torsion bar disposed on the upper sample assembly and being torsional upon the rotation of the upper sample assembly; and
an optical torque measuring assembly configured to measure a torsion angle of the torsion bar so as to obtain a torque generated during shearing the fluid to be tested,
wherein the lower sample assembly comprises:
a lower sample connector disposed on the driving device; and
a lower sample disposed on the lower sample connector, the fluid to be tested being disposed on an upper surface of the lower sample,
wherein two spaced supporting pillars are disposed on the upper surface of the lower sample connector and extend upwards from the upper surface of the lower sample connector, and a supporting platform having a spherical upper surface is disposed between the two supporting pillars;
wherein two mounting grooves are disposed in the lower surface of the lower sample and configured to cooperate with the two supporting pillars respectively, and the lower surface of the lower sample abuts against the upper surface of the supporting platform.

10. The rheometer of claim 9, wherein the lower sample is fixedly connected with the lower sample connector, and the upper sample assembly comprises:
an upper sample having an upper surface and a lower surface contacted with the fluid to be tested; and
an upper sample connector defining two ends connected with the upper surface of the upper sample and a lower surface of the torsion bar respectively,
wherein the upper sample connector connected with the lower surface of the torsion bar, two spaced supporting bars being disposed on the lower surface of the upper sample connector and extend downwards from the lower surface of the upper sample connector, a supporting ball having a spherical lower surface being disposed between the two supporting bars; and
the upper sample having two connecting grooves in an upper surface thereof and configured to cooperate with the two connecting bars respectively, a receiving groove being provided between the two connecting grooves and configured to cooperate with the supporting ball, the two supporting bars being inserted in the two connecting grooves respectively and the supporting ball being received in the receiving groove, the upper sample being connected with the upper sample connector if the lower surface of the upper sample is flush with the upper surface of the lower sample.

11. The rheometer of claim 10, wherein a process of assembling the upper sample and the upper sample connector comprises:
attaching the lower surface of the upper sample to the upper surface of the lower sample, such that the lower surface of the upper sample is parallel to the upper surface of the lower sample;
contacting the upper sample connector with the upper sample, such that the supporting bars are inserted in the connecting grooves respectively and the supporting ball is received in the receiving groove; and
fixedly connecting the upper sample to the upper sample connector, and moving the upper sample connector upwards to remove the upper sample from the lower sample.

12. The rheometer of claim 10, wherein the upper sample is fixedly connected with the upper sample connector via a binder.

13. The rheometer of claim 12, wherein the binder comprises glue.

* * * * *